US006139846A

United States Patent [19]
Forsgren

[11] Patent Number: 6,139,846
[45] Date of Patent: Oct. 31, 2000

[54] PROTEIN D- AN IGD-BINDING PROTEIN OF HAEMOPHILUS INFLUENZAE

[76] Inventor: Arne Forsgren, Sothönsvagen 4 B, S-230 11 Falsterbo, Sweden

[21] Appl. No.: 09/225,443

[22] Filed: Jan. 6, 1999

Related U.S. Application Data

[62] Division of application No. 08/936,912, Sep. 25, 1997, Pat. No. 5,888,517, which is a continuation of application No. 08/468,618, Jun. 6, 1995, abandoned, which is a continuation of application No. 07/946,499, Nov. 9, 1992, abandoned.

[30] Foreign Application Priority Data

May 31, 1990 [SE] Sweden .................................. 9001949
Feb. 21, 1991 [WO] WIPO ...................... PCT/SE91/00129

[51] Int. Cl.[7] ........................ A61K 39/102; A61K 39/00; A61K 39/38; C07K 1/00; C07K 14/00
[52] U.S. Cl. .................................... 424/256.1; 424/184.1; 424/185.1; 530/350; 436/513
[58] Field of Search ............................. 424/256.1, 184.1, 424/185.1; 530/350; 436/513

[56] References Cited

U.S. PATENT DOCUMENTS 3,800,798  4/1974  Winkler .
3,995,018  11/1976  Sjöquist .

FOREIGN PATENT DOCUMENTS

| | | |
|---|---|---|
| 0 131 142 | 1/1985 | European Pat. Off. . |
| 0 200 909 | 12/1986 | European Pat. Off. . |
| 0 281 673 | 9/1988 | European Pat. Off. . |
| 0 320 289 | 6/1989 | European Pat. Off. . |
| 9001949 | 5/1990 | Sweden . |
| 87/05631 | 9/1987 | WIPO . |

OTHER PUBLICATIONS

Loeb et al, "Protection of infant rats from . . . ", InfecT. and Imm. 55(11):2612–2618, 1987.
Dashefsky et al, "Safety, Tolerability and . . . ", Pediatrics Suppl., 85(4):682–689, part 2, 1990.
Janson et al, "Protein D, the Immunoglobin D–Binding Protein", Infect. and Imm. 60:1336–1342, 1992.
Murphy et al, "Nontypable Haemophilus Influenzae", Review Infect. Diseases, 9:1–15, 1987.
Munson, Jr. et al., "Purification and Comparison of Outer Membrane Protein P2 . . . ", J. Chem. Invest., 72:677–684, 1983.
Munson, Jr. et al., Purification and Partial Characterization of Outer Membrane Proteins P5 . . . Infect. and Imm. 49:544–549, 1985.
Kimura et al, "A Minor High–Molecular–Weight Outer Membrane Protein . . . ", Infect. and Imm., 47(1):253–259, 1985.
Murphy et al, "A Subtyping System for Nontypable . . . Proteins", J. of Infectious Diseases, 147(5):838–846, 1983.
Weber et al, "The Reliability of Molecular Weight Determinations by Dodecyl Sulfate–Polyacrylamide Gel Electrophoresis", The J. of Biol. Chem., 244(16):4406–4412, 1969.
Clark–Curtiss et al, Molecular Analysis of DNA and Construction of Genomic Libraries . . . , J. of Bacteriol., 161(3):1093–1102, 1985.
Shine et al., "The 3'–Terminal Sequence of *Eschericia coli* 16S Ribosomal RNA . . . ", Proc. Nat. Acad. Sci., U.S.A., 71(4):1342–1346, 1974.
Vlasuk et al, "Effects of Complete Removal of Basic Amino Acid Residues from the Signal Peptide . . . ", J. of Biol. Chem., 258(11):7141–7148, 1983.
Forsgren et al, "Many Bacterial Species Bind Human IgD", J. of Immunol.., 122(4):1468–1472, 1979.
Janson et al, "Protein D, an Immunogloblin D–Binding Protein . . . ", Infect. and Imm., 59(1):119–125, 1991.
Ruan et al, "Protein D of *Haemophilus influenzae*: A Novel Bacterial Surface . . .", J. of Immunol., 145(10):3379–3384, 1990.
Lenser et al, Vet. Microbiol., 18(3–4):335–348, 1988.
Munson et al, J. Bact., 175(14):4569–4571, 1993.
Larson et al, Arch. Biochem. Biophys., 260(2):577–584, 1988.
Sasaki et al, Infect. and Imm., 61(7):3026–3031, 1993.
Fedorka–Crey et al, Infect. and Imm., 58(2):358–365, 1990.
Loeb et al, Pediatr. Infect. Dis. J., 8(1 suppl.)548–550.
Janson et al, Abstr. on Meet. Am. Soc. Microbiol., 92:136, 1992.
Dashefsky et al, Pediatrics, 84:682–689 (Apr., 1970).
Jansen et al.; Protein D, an immunoglobulin D–binding protein of . . . ; Infection and Immunity ; vol. 59, No. 1; pp. 119–125, Jan. 1991.
Allen et al.; Molecular structure of mammalian neuropeptide Y . . . ; Proceedings of the National Academy of the Sciences; vol. 84; pp. 2532–2536, Apr. 1987.

*Primary Examiner*—Jeffrey Stucker
*Assistant Examiner*—Brett Nelson
*Attorney, Agent, or Firm*—Burns, Doane, Swecker & Mathis, L.L.P.

[57] ABSTRACT

A novel surface exposed protein of *Haemophilus influenzae* or related Haemophilus species is described. The protein named protein D is an Ig receptor for human IgD and has an apparent molecular weight of 42,000. Protein D can be detected in all of 116 encapsulated and non-encapsulated isolates of *H. influenzae* studied. The protein from all strains shows in addition to the same apparent molecular weight immunogenic similarities since protein D from all strains interacts with three different mouse monoclonal antibodies and monoclonal human IgD. A method for purification of protein D is described. Cloning of the protein D gene from *H. influenzae* in *E. coli* is described as well as the nucleotide sequence and the deduced amino acid sequence.

8 Claims, 13 Drawing Sheets

Percent of $^{125}I$ IgD Binding

```
108  AAAAAAGGCGGTGGGCAAATTGCTTAGTCGCCCTTTTTTGTAACTAAAAATCTAAAAACTCT  167
                                  -----                        -----
                                   -35                          -10

168  ATAAAAATTTACCGCACTCTTAAGGAGAAATACTTATGAAACTTAAAACTTAGCCCTT  227
                         ======      MetLysLeuLysThrLeuAlaLeu
                           rbs 228  TCTTTATTAGCAGCTGGCGTACTAGCAGGTTGTAGCAGCCATTCATCAAATATGGCGAAT  287
     SerLeuLeuAlaAlaGlyValLeuAlaGlyCysSerSerHisSerSerAsnMetAlaAsn 288  ACCCAAATGAAATCAGACAAAATCATTATTGCTCACCGTGGTGCTAGCGGTTATTTACCA  347
     ThrGlnMetLysSerAspLysIleIleIleAlaHisArgGlyAlaSerGlyTyrLeuPro 348  GAGCATACGTTAGAATCTAAAGCACTTGCGTTTGCACAACAGGCTGATTATTTAGAGCAA  407
     GluHisThrLeuGluSerLysAlaLeuAlaPheAlaGlnGlnAlaAspTyrLeuGluGln 408  GATTTAGCAATGACTAAGGATGGTCGTTTAGTGGTTATTCACGATCACTTTTTAGATGGC  467
     AspLeuAlaMetThrLysAspGlyArgLeuValValIleHisAspHisPheLeuAspGly 468  TTGACTGATGTTGCGAAAAATTCCCACATCGTCATCGTAAAGATGGCCGTTACTATGTC  527
     LeuThrAspValAlaLysLysPheProHisArgLysAspGlyArgTyrTyrVal
```

FIG. 9A-1

```
528  ATCGACTTTACCTTTAAAAGAAATTCAAAGTTTAGAAAATGACAGAAAACTTTGAAACCAAA  587
     IleAspPheThrLeuLysGluIleGlnSerLeuGluMetThrGluAsnPheGluThrLys

588  GATGGCAAACAAGGCAAGTTTATCCTAATCGTTTCCCTCTTTGGAAATCACATTTTAGA  647
     AspGlyLysGlnAlaGlnValTyrProAsnArgPheProLeuTrpLysSerHisPheArg

648  ATTCATACCTTTGAAGATGAAATTGAATTTATCCAAGGCTTAGAAAAATCCACTGGCAAA  707
     IleHisThrPheGluAspGluIleGluPheIleGlnGlyLeuGluLysSerThrGlyLys

708  AAAGTAGGGATTTATCCAGAAATCAAAGCACCTTGGTTCCACCATCAAAATGGTAAAGAT  767
     LysValGlyIleTyrProGluIleLysAlaProTrpPheHisHisGlnAsnGlyLysAsp
```

FIG. 9A-2

```
768  ATTGCTGCTGAAACGCTCAAAGTGTTAAAAAAATATGGCTATGATAAGAAACCGATATG 827
     IleAlaAlaGluThrLeuLysValLeuLysLysTyrGlyTyrAspLysLysThrAspMet

828  GTTTACTTACAAACTTTCGATTTTAATGAATTAAAAACGTATCAAAACGGAATTACTTCCA 887
     ValTyrLeuGlnThrPheAspPheAsnGluLeuLysThrTyrGlnThrGluLeuLeuPro

888  CAAATGGGAATGGATTTGAAATTAGTTCAATTAATTGCTTATACAGATTGGAAAGAAACA 947
     GlnMetGlyMetAspLeuLysLeuValGlnLeuIleAlaTyrThrAspTrpLysGluThr

948  CAAGAAAAAGACCCAAAGGGTTATTGGGTAAACTATAATTACGATTGGATGTTTAAACCT 1007
     GlnGluLysAspProLysGlyTyrTrpValAsnTyrAsnTyrAspTrpMetPheLysPro

1008 GGTGCAATGGCAGAAGTGGTAAATATGCCGATGGTGTTGGCCCAGGTTGGTATATGTTA 1067
     GlyAlaMetAlaGluValValAsnMetProMetValLeuAlaGlnValGlyTyrMetLeu

1068 GTTAATAAAGAAGAATCCAAACCTGATAATATTGTGTACACTCCGTTGGTAAAAGAACTT 1127
     ValAsnLysGluGluSerLysProAspAsnIleValTyrThrProLeuValLysGluLeu

1128 GCACAATATAATGTGGAAGTGCATCCTTACACCGTGCGTAAAGATGCACTGCCCGAGTTT 1187
     AlaGlnTyrAsnValGluValHisProTyrThrValArgLysAspAlaLeuProGluPhe
```

FIG. 9B-1

```
1188  TTCACAGACGTAAATCAAATGTATGATGCCTTATTGAATAAATCAGGGCAACAGGTGTA  1247
      PheThrAspValAsnGlnMetTyrAspAlaLeuLeuAsnLysSerGlyAlaThrGlyVal

1248  TTTACTGATTTCCCAGATACTGGCGGTGGAATTCTTAAAAGGAATAAAATAATATCCCTCA  1307
      PheThrAspPheProAspThrGlyValGluPheLeuLysGlyIleIleLysEnd

1308  CAACCGTGGGTAAACATACCCACGGTTAACTAGGTTTCTATATCGTAGAAACTAAAAATC  1367
```

FIG. 9B-2

1. H. influenzae
2. E.coli pHIC348 (cytoplasmic fraction)
3. E.coli pHIC348 (periplasmic fraction)
4. E.coli pHIC348 (membrane fraction)

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 1260 base pairs
        (B) TYPE: nucleic acid
        (C) STRANDEDNESS: single
        (D) TOPOLOGY: unknown (ii) MOLECULE TYPE: DNA (genomic)

(ix) FEATURE:
        (A) NAME/KEY: CDS
        (B) LOCATION: 97..1188

(xi) SEQUENCE DESCRIPTION: SEQ ID NO:1:

```
AAAAAGGCG GTGGGCAAAT TGCTTAGTCG CCTTTTTTGT AACTAAAATC TAAAAACTCT          60

ATAAAATTT ACCGCACTCT TAAGGAGAAA ATACTT ATG AAA CTT AAA ACT TTA          114
                                      Met Lys Leu Lys Thr Leu
                                        1               5

GCC CTT TCT TTA TTA GCA GCT GGC GTA CTA GCA GGT TGT AGC AGC CAT          162
Ala Leu Ser Leu Leu Ala Ala Gly Val Leu Ala Gly Cys Ser Ser His
             10                  15                  20

TCA TCA AAT ATG GCG AAT ACC CAA ATG AAA TCA GAC AAA ATC ATT ATT          210
Ser Ser Asn Met Ala Asn Thr Gln Met Lys Ser Asp Lys Ile Ile Ile
         25                  30                  35

GCT CAC CGT GGT GCT AGC GGT TAT TTA CCA GAG CAT ACG TTA GAA TCT          258
Ala His Arg Gly Ala Ser Gly Tyr Leu Pro Glu His Thr Leu Glu Ser
     40                  45                  50

AAA GCA CTT GCG TTT GCA CAA CAG GCT GAT TAT TTA GAG CAA GAT TTA          306
Lys Ala Leu Ala Phe Ala Gln Gln Ala Asp Tyr Leu Glu Gln Asp Leu
 55                  60                  65                  70

GCA ATG ACT AAG GAT GGT CGT TTA GTG GTT ATT CAC GAT CAC TTT TTA          354
Ala Met Thr Lys Asp Gly Arg Leu Val Val Ile His Asp His Phe Leu
                 75                  80                  85

GAT GCC TTG ACT GAT GTT GCG AAA AAA TTC CCA CAT CGT CAT CGT AAA          402
Asp Ala Leu Thr Asp Val Ala Lys Lys Phe Pro His Arg His Arg Lys
             90                  95                 100

GAT GGC CGT TAC TAT GTC ATC GAC TTT ACC TTA AAA GAA ATT CAA AGT          450
Asp Gly Arg Tyr Tyr Val Ile Asp Phe Thr Leu Lys Glu Ile Gln Ser
         105                 110                 115

TTA GAA ATG ACA GAA AAC TTT GAA ACC AAA GAT GGC AAA CAA GCG CAA          498
Leu Glu Met Thr Glu Asn Phe Glu Thr Lys Asp Gly Lys Gln Ala Gln
     120                 125                 130
```

```
GTT TAT CCT AAT CGT TTC CCT CTT TGG AAA TCA CAT TTT AGA ATT CAT      546
Val Tyr Pro Asn Arg Phe Pro Leu Trp Lys Ser His Phe Arg Ile His
135                 140                 145                 150

ACC TTT GAA GAT GAA ATT GAA TTT ATC CAA GGC TTA GAA AAA TCC ACT      594
Thr Phe Glu Asp Glu Ile Glu Phe Ile Gln Gly Leu Glu Lys Ser Thr
            155                 160                 165

GGC AAA AAA GTA GGG ATT TAT CCA GAA ATC AAA GCA CCT TGG TTC CAC      642
Gly Lys Lys Val Gly Ile Tyr Pro Glu Ile Lys Ala Pro Trp Phe His
                170                 175                 180

CAT CAA AAT GGT AAA GAT ATT GCT GCT GAA ACG CTC AAA GTG TTA AAA      690
His Gln Asn Gly Lys Asp Ile Ala Ala Glu Thr Leu Lys Val Leu Lys
            185                 190                 195

AAA TAT GGC TAT GAT AAG AAA ACC GAT ATG GTT TAC TTA CAA ACT TTC      738
Lys Tyr Gly Tyr Asp Lys Lys Thr Asp Met Val Tyr Leu Gln Thr Phe
200                 205                 210

GAT TTT AAT GAA TTA AAA CGT ATC AAA ACG GAA TTA CTT CCA CAA ATG      786
Asp Phe Asn Glu Leu Lys Arg Ile Lys Thr Glu Leu Leu Pro Gln Met
215                 220                 225                 230

GGA ATG GAT TTG AAA TTA GTT CAA TTA ATT GCT TAT ACA GAT TGG AAA      834
Gly Met Asp Leu Lys Leu Val Gln Leu Ile Ala Tyr Thr Asp Trp Lys
                235                 240                 245

GAA ACA CAA GAA AAA GAC CCA AAG GGT TAT TGG GTA AAC TAT AAT TAC      882
Glu Thr Gln Glu Lys Asp Pro Lys Gly Tyr Trp Val Asn Tyr Asn Tyr
            250                 255                 260

GAT TGG ATG TTT AAA CCT GGT GCA ATG GCA GAA GTG GTT AAA TAT GCC      930
Asp Trp Met Phe Lys Pro Gly Ala Met Ala Glu Val Val Lys Tyr Ala
                265                 270                 275

GAT GGT GTT GGC CCA GGT TGG TAT ATG TTA GTT AAT AAA GAA GAA TCC      978
Asp Gly Val Gly Pro Gly Trp Tyr Met Leu Val Asn Lys Glu Glu Ser
280                 285                 290

AAA CCT GAT AAT ATT GTG TAC ACT CCG TTG GTA AAA GAA CTT GCA CAA     1026
Lys Pro Asp Asn Ile Val Tyr Thr Pro Leu Val Lys Glu Leu Ala Gln
295                 300                 305                 310

TAT AAT GTG GAA GTG CAT CCT TAC ACC GTG CGT AAA GAT GCA CTG CCC     1074
Tyr Asn Val Glu Val His Pro Tyr Thr Val Arg Lys Asp Ala Leu Pro
                315                 320                 325

GAG TTT TTC ACA GAC GTA AAT CAA ATG TAT GAT GCC TTA TTG AAT AAA     1122
Glu Phe Phe Thr Asp Val Asn Gln Met Tyr Asp Ala Leu Leu Asn Lys
            330                 335                 340

TCA GGG GCA ACA GGT GTA TTT ACT GAT TTC CCA GAT ACT GGC GTG GAA     1170
Ser Gly Ala Thr Gly Val Phe Thr Asp Phe Pro Asp Thr Gly Val Glu
                345                 350                 355

TTC TTA AAA GGA ATA AAA TAATATCCCT CACAACCGTG GGTAAACATA            1218
Phe Leu Lys Gly Ile Lys
            360

CCCACGGTTA ACTAGGTTTC TATATCGTAG AAACTAAAAA TC                      1260

(2) INFORMATION FOR SEQ ID NO:2:

(i) SEQUENCE CHARACTERISTICS:
        (A) LENGTH: 4 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:2:

Leu Ala Gly Lys
```

PROTEIN D- AN IGD-BINDING PROTEIN OF HAEMOPHILUS INFLUENZAE

This application is a divisional of application Ser. No. 08/936,912, filed Sep. 25, 1997, now U.S. Pat. No. 5,888,517, which is a continuation of application Ser. No. 08/468,618, filed Jun. 6, 1995, now abandoned which is a continuation of application Ser. No. 07/946,499, filed Nov. 9, 1992, now abandoned which is based upon PCT/SE91/00129, filed Feb. 21, 1991.

The present invention is related to a surface exposed protein named protein D which is conserved in many strains of *Haemophilus influenzae* or related Haemophilus species. Protein D is an Ig receptor for human IgD.

Several immunoglobulin (Ig) binding bacterial cell wall proteins have been isolated and/or cloned during the last two decades. The best characterized of these are protein A of *Staphylococcus aureus* and protein G of group G beta-hemolytic streptococci. The classical Fc-binding capacity of protein A involves IgG from humans and several mammalian species but the binding is restricted to human IgG subclasses 1, 2 and 4. Also other human classes of Ig (G, A, M, E) have been shown to bind to protein A, a reactivity that has been designed the alternative Ig binding which is mediated by Fab structures and characterized by a variable occurrence in the different Ig classes.

Protein G of group G streptococci binds all human IgG subclasses and has also a wider binding spectrum for animal IgG than protein A. On the IgG molecule the Fc part is mainly responsible for the interaction with protein G although a low degree of interaction was also recorded for Fab fragments. IgM, IgA and IgD, however, show no binding to protein G. Both protein A and protein G have acquired many applications for immunoglobulin separation and detection. (EP 0 200 909, EP 0 131 142, WO 87/05631, U.S. Pat. Nos. 3,800,798, 3,995,018.)

Certain strains of group A streptococci are also known to produce an IgG-binding protein which has been purified or cloned. The Ig-binding protein from group A streptococci is relatively specific for human IgG. Information about bacterial molecules that selectively bind IgA and IgM is more limited. However, IgA-binding proteins have been isolated from both group A and group B streptococci, two frequent human pathogens. The IgA receptor of group A streptococci has been named protein Arp. Certain strains of the anaerobic bacterium *Clostridium perfringens* preferentially bind IgM but also IgA and IgG. This binding is due to a cell surface protein (protein P). Recently a bacterial protein, protein L, with unique binding properties for L-chains was isolated from *Peptococcus magnus*. Protein L has been shown to bind IgG, IgA and IgM from human and several mammalian species. Among gram-negative bacteria, Ig receptors have been reported among veterinary pathogens. Brucella abortus binds bovine IgM and Taylorella equigenitalis, a venereal pathogen of horses, binds equine IgG. Recently *Haemophilus somnus* was reported to bind bovine IgG.

A decade ago *Haemophilus influenzae* and *Moraxella* (*Branhamella*) *catarrhalis* were shown to have a high binding capacity for human IgD (Forsgren A. and Grubb A, J. Immunol. 122:1468, 1979).

The present invention describes the solubilization and purification of a *H. influenzae* surface protein responsible for the interaction with IgD. It also describes the cloning, expression and nucleotide sequence of the IgD-binding protein gene of the *H. influenzae* in *Escherichia coli*. In addition it describes the Ig-binding properties of this molecule, named protein D, which were found to be different compared with previously isolated Ig-binding proteins. Protein D was found only to interact with IgD and not with other human immunoglobulin classes. Thus, protein D could be an important tool for studies, separation and detection of IgD in a way similar to the way in which protein A and protein G previously have been used for IgG. Protein D could also be a valuable tool alone and in combination with other molecules (for example proteins and polysaccharides) in the stimulation of the immune system through an interaction with B-lymphocytes. Protein D is not identical with any previously described protein from *H. influenzae*.

*H. influenzae* is a common human parasite and pathogen which colonizes the mucosa of the upper respiratory tract and causes disease by local spread or invasion. An important distinguishing feature between *H. influenzae* isolates is whether or not they are encapsulated. Encapsulated *H. influenzae* type b is a primary cause of bacterial meningitis and other invasive infections in children under 4 years of age in Europe and the United States. Non-encapsulated (non-typable) *H. influenzae* rarely cause invasive infection in healthy children and adults but are a frequent cause of otitis media in children and have been implicated as a cause of sinusitis in both adults and children. *H. influenzae* are also commonly isolated in purulent secretions of patients with cystic fibrosis and chronic bronchitis and have recently been recognized as an important cause of pneumonia.

A vaccine composed of purified type b capsular polysaccharide has proven effective against *H. influenzae* type b disease in children of 2 to 5 years of age. However, since children under two years of age respond poorly to this vaccine, conjugate vaccines with enhanced immunogenicity have been developed by covalently bonding the capsular polysaccharide to certain proteins. However, the polysaccharide vaccines, non-conjugated and conjugated, are of no value against nontypable *H. influenzae* disease. Hence, other cell surface components and in particular outer membrane proteins (OMPs) have been looked at as potential vaccine candidates both against type b and nontypable *H. influenzae*. (EP 0 281 673, EP 0 320 289.)

The outer membrane of *H. influenzae* is typical of gram-negative bacteria and consists of phospholipids, lipopolysaccharide (LPS), and about 24 proteins. Four different Haemophilus OMPs have been shown to be targets for antibodies protective against experimental Haemophilus disease. These include the P1 heat-modifiable major outer membrane protein, the P2 porin protein, the P6 lipoprotein and a surface protein with an apparent molecular weight of 98,000 (98 K protein). Of these at least antibodies to P2 have been shown not to protect against challenge with heterologous Haemophilus strains. (Loeb, M. R. Infect. Immun. 55:2612, 1987; Munson Jr, R. S. et al J. Clin. Invest. 72:677, 1983; Munson Jr, R. S. and Granoff, D. M. Infect. Immun. 49:544, 1985 and Kimura, A. et al, Infect. Immun. 194:495, 1985).

Analysis of nontypable *H. influenzae* has shown that there are marked differences in OMP composition among strains (See e.g. Murphy et al. "A subtyping system for nontypable *Haemophilus influenzae* based on outer membrane proteins" J Infect Dis 147:838, 1983; Barenkamp et al. "Outer membrane protein and biotype analysis of pathogenic nontypable *Haemophilus influenzae*" Infect Immun 30:709, 1983).

If a surface exposed antigen (immunogen) which is conserved in all strains of *H. influenzae* could be found it would be an important tool in developing a method of identifying *H. influenzae* in clinical specimens as well as a vaccine against *H. influenzae*. The present invention shows that protein D with an identical apparent molecular weight (42,000), reacting with three different monoclonal antibodies and human IgD, was found in all 116 *H. influenzae* strains (encapsulated and nonencapsulated) studied, as well as in two other related Haemophilus species, namely *H. haemolyticus* and *H. aegypticus*.

Thus, according to the invention there is provided a surface exposed protein, which is conserved in many strains of *Haemophilus influenzae* or related Haemophilus species, having an apparent molecular weight of 42,000 and a capacity of binding human IgD. The invention also comprises naturally occurring or artificially modified variants of said protein, and also immunogenic or IgD-binding portions of said protein and variants. The protein is named protein D and has the amino acid sequence depicted in FIG. 9 (SEQ ID NO: 2).

There is also provided a plasmid or phage containing a genetic code for protein D or the above defined variants or portions.

Further there is provided a non-human host containing the above plasmid or phage and capable of producing said protein or variants, or said portions thereof. The host is chosen among bacteria, yeasts or plants. A presently preferred host is *E. coli*.

In a further aspect the invention provides for a DNA segment comprising a DNA sequence which codes for protein D, or said variants thereof, or for said portions. The DNA sequence is shown in FIG. 9 (SEQ ID NO: 1).

In yet another aspect, the invention provides for a recombinant DNA molecule containing a nucleotide sequence coding for protein D, or said variants or portions, which nucleotide sequence could be fused to another gene.

A plasmid or a phage containing the fused nucleotide defined above could also be constructed.

Further such a plasmid or phage could be inserted in a non-human host, such as bacteria, yeasts or plants. At present, *E. coli* is the preferred host.

The invention also comprises a fusion protein or polypeptide in which protein D, or said variants or portions, could be combined with another protein by the use of a recombinant DNA molecule, defined above.

Furthermore, a fusion product in which protein D, or said variants or portions, is covalently or by any other means bound to a protein, carbohydrate or matrix (such as gold, "Sephadex" particles, polymeric surfaces) could be constructed.

The invention also comprises a vaccine containing protein D, or said variants or portions. Other forms of vaccines contain the same protein D or variants or portions, combined with another vaccine, or combined with an immunogenic portion of another molecule.

There is also provided a hybridoma cell capable of producing a monoclonal antibody to an immunogenic portion of protein D, or of naturally occurring or artificially modified variants thereof.

Further there is provided a purified antibody which is specific to an immunogenic portion of protein D or of naturally ooccurring or artificially modified variants thereof. This antibody is used in a method of detecting the presence of *Haemophilus influenzae* or related Haemophilus species in a sample by contacting said sample with the antibody in the presence of an indicator.

The invention also comprises a method of detecting the presence of *Haemophilus influenzae* or related Haemophilus species in a sample by contacting said sample with a DNA probe or primer constructed to correspond to the nucleic acids which code for protein D, or for naturally occurring or artificially modified variants thereof, or for an immunogenic or IgD-binding portion of said protein or variants.

Protein D, or said variants or portions, is also used in a method of detecting IgD. In such a detecting method the protein may be labelled or bound to a matrix.

Finally, the invention comprises a method of separating IgD using protein D, or said variants or portions, optionally bound to a matrix.

BRIEF DESCRIPTION OF THE DRAWINGS

FIGS. 9a and 9b are a DNA sequence (SEQ ID NO:1) which reveals an optic reading frame of 1092 bp starting with an ATG codon at position 204 and finishing at position 1296 with TAA stop codon.

DETAILED DESCRIPTION OF THE INVENTION

Materials and Methods

Bacteria

Figure 1:
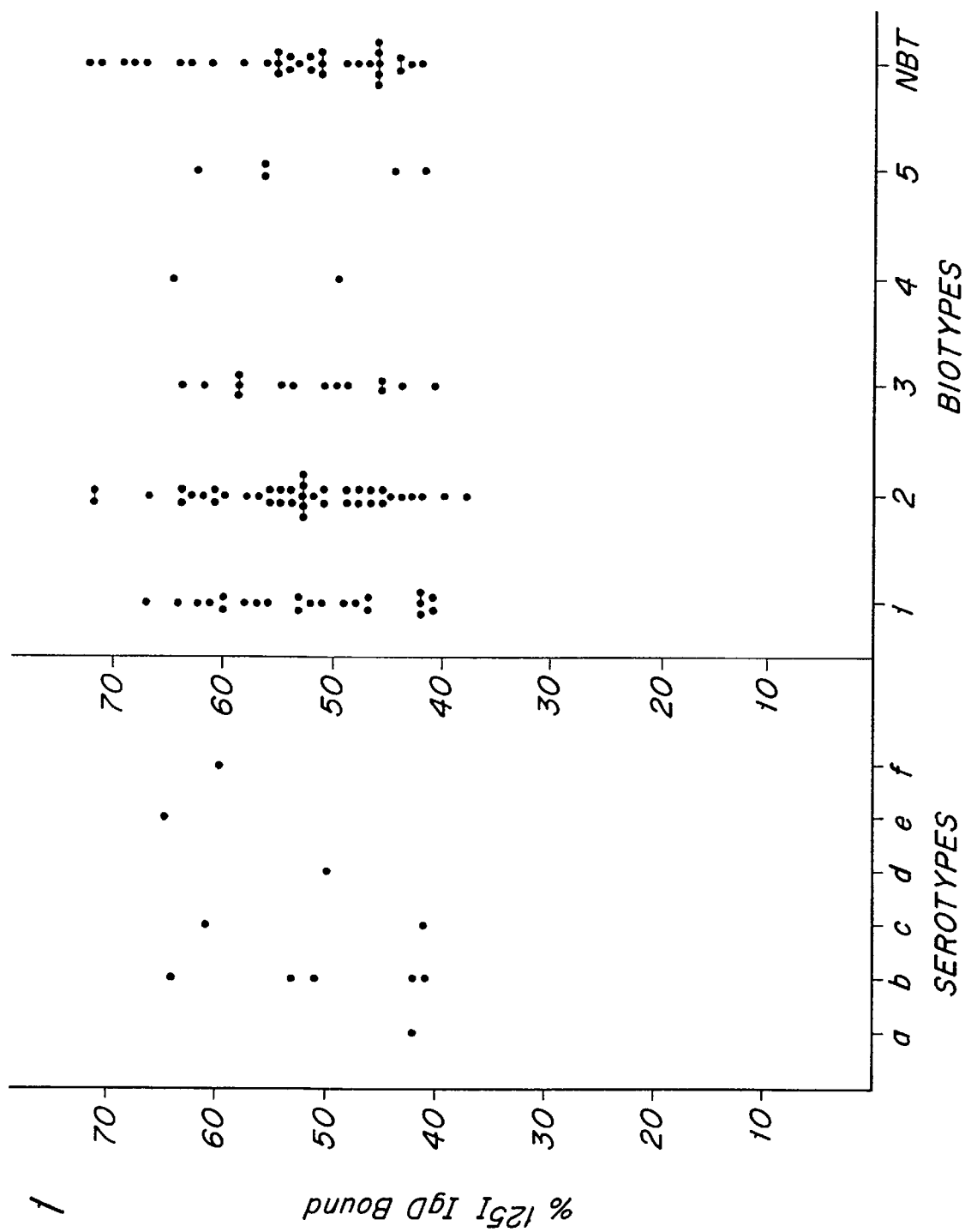
FIG. 1 is a graph of % $^{125}$I-IgD bound versus serotypes and biotypes showing that all *H. Influenzae* isolates bound IgD to a high degree.

116 *H. influenzae* strains representing serotypes a–f and nontypable and in addition bacterial strains representing 12 species related to *H. influenzae* were obtained from different laboratories in Denmark, Sweden and the U.S.A.

Culture Conditions

All strains of Haemophilus, Ekinella and Acinobacillus were grown on chocolate agar. *H. ducreyi* were grown in microaerophilic atmosphere at 37° C. and all other *Haemophilus strains* in an atmosphere containing 5% $CO_2$. 30 isolates of *H. influenzae* were also grown overnight at 37° C. in brain-heart infusion broth (Difco Lab., Inc. Detroit, Mich.) supplemented with nicotinamide adenine dinucleotide and hemin (Sigma Chemical Co. St Louis, Mo.), each at 10 µg/ml.

Immunoglobulins and Proteins

IgD myeloma proteins from four different patients were purified as described (Forsgren, A. and Grubb, A., J. Immunol. 122:1468, 1979). Eight different human IgG myeloma proteins representing all four subclasses and both L-chain types, three different IgM myeloma proteins and one IgA myeloma protein were isolated and purified according to standard methods. Human polyclonal IgG, serum albumin and plasminogen were purchased from Kabi Vitrum AB, Stockholm, Sweden, and human IgE was adapted from Pharmacia IgE RIACT kit (Pharmacia Diagnostic AB, Uppsala, Sweden). Bovine serum albumin, human and bovine fibrinogen and human transferrin were purchased or obtained as a gift.

$^{125}$I-IgD Binding Assay

The binding assay was carried but in plastic tubes. Briefly $4 \times 10^8$ bacterial cells in a volume of 100 μl phosphate buffered saline (PBS) with the addition of 5% human serum albumine (HSA) were mixed with 100 μl of $^{125}$I-IgD in the same buffer (radioactivity was adjusted to $7-8 \times 10^4$ cpm, i.e approx. 40 ng). After 0.5 h incubation at 37° C., 2 ml of ice-cold PBS (containing 0.1% Tween 20) was added to the tubes.

The suspension was centrifugated at 4,599×g for 15 min and the supernatant was aspirated. Radioactivity retained in the bacterial pellet was measured in a gamma counter (LKB Wallac Clingamma 1271, Turku, Finland). Residual radioactivity from incubation mixtures containing no bacteria, i.e. background, was 2.5 percent. Samples were always tested in triplicates and each experiment was repeated at least twice, unless otherwise stated.

Monoclonal Antibodies

Inbred female BALB/c mice (age 8 to 14 weeks) were immunized by an intraperitoneal injection of 25 μg purified protein D (25 μg/50 μl) in Freund's complete adjuvant (300 μl) followed by two intraperitoneal injections of protein D (15 μg) in Freund's incomplete adjuvant (300 μl) 3 and 7 weeks later. In week 9 the mice were bled from the tails, serum was separated and tested for anti-protein D activity in an enzyme-linked immuno-sorbent assay (ELISA). The best responding mouse was boosted by an intravenous injection of protein D (2 μg) in 150 μl PBS. One day after the last injection, the spleen was excised and spleen cells were prepared for the production of monoclonal antibodies (De St Groth S F, Scheidegger S J J Immunol Methods 35:1, 1980). After 10 to 14 days (mean 12 days) the hybridomas were tested for the production of antibodies against protein D in an enzyme-linked immunosorbent assay (ELISA), and the hybrids producing the highest titers of antibodies were cloned and expanded by cultivation in RPMI medium containing 10% fetal bovine serum. Totally 68 clones producing antibodies to protein D were obtained. Three of the hybridomas were selected for further growth in the same medium. All cell lines were frozen in the presence of dimethyl sulfoxide and 90% fetal bovine serum in liquid nitrogen.

SDS-PAGE and Detection of Protein D on Membranes

SDS-PAGE was, using a modified Laemmli gel, prepared and run according to the procedure of Lugtenberg et al., (FEBS Lett 58:254, 1975) using a total acrylamide concentration of 11%. Samples of crude Sarcosyl extracts of *H. influenzae* and related bacterial species were pretreated by 5-min boiling in sample buffer consisting of 0.06M of Tris hydrochloride (pH 6.8), 2% (w/v) SDS, 1% (v/v) β-ME, 10% glycerol, and 0.03% (w/v) bromphenol blue. Electrophoresis was performed at room temperature using PROTEIN II vertical slab electrophoresis cells (Bio-Rad Laboratories, Richmond, Calif.) at 40 mA per gel constant current. Staining of proteins in gels was done with comassie brilliant blue in a mixture of methanol, acetic acid and water essentially as described by Weber and Osborn (J. Biol. Chem. 244:4406, 1969). Protein bands were also transferred to nitrocellulose membranes (Sartorius, West Germany) by electrophoretic transfer from SDS-polyacrylamide gels. Electrophoretic transfer was carried out in a Trans-Blot Cell (Bio-Rad) at 50 V for 90 min. The electrode buffer was 0.025M Tris, pH 8.3, 0.192M glycine, and 20% methanol. The membranes were then washed for 1 h at room temperature in 1.5% ovalbumin-Tris balanced saline (OA-TBS), pH 7.4, to saturate additional binding sites.

After several washings with Tris balanced saline (TBS), the membranes were incubated overnight at room temperature in 1% OA-TBS buffer containing IgD (20 μg/ml) to detect IgD-binding bands, then washed twice with TBS. The membranes were then incubated with peroxidase conjugated goat anti-human IgD (Fc) (Nordic Immunology, Tiiburg, The Netherlands) for 1–2 hrs at room temperature; after several washings with Tween-TBS the membranes were developed with 4-chloro-1-napthol and hydrogen peroxide. Protein D was also identified using anti-protein D mouse monoclonal antibodies 16ClO, 20G6 and 19B4 at 1:50 dilution in 1% OA-TBS. Protein 1 and 2 of *H. influenzae* were identified using anti-P2 mouse monoclonal 9F5 (Dr. Eric J. Hansen, Dallas, Tex., U.S.A.) at a 1:1000 dilution and rabbit anti-P1 serum (Dr. Robert S. Munson, St. Louis, Mo., U.S.A.) at a 1:200 dilution.

Solubilization and Purification of Protein D from *H. influenzae*

Briefly 3 g of bacteria were suspended in 10 ml of 10 mM HEPES Tris buffer (pH 7.4) containing 0.01M EDTA and sonicated three times in a sonifier (MSE) for 1 min while cooling in an ice bath. Following sonication Sarcosyl (Sodium Lauryl Sarcosinate) was added to a final concentration of 1% (w/v). The suspensions were incubated at room temperature for 1 h using a shaker and then sonicated gain 2×1 min on ice and reincubated at room temperature or 30 min. After centrifugation at 12,000 g for 15 min at 4° C. the supernatant was harvested and recentrifugated at 105,000 g for 1.5 h at 4° C.

Sarcosylextracts prepared of *H. influenzae*, strain NT 772 as described above were applied to SDS-PAGE. After electrophoresis narrow gel strips were cut out, protein was transferred to membranes and the IgD-binding band was detected by Western blot assay using IgD and peroxidase conjugated goat anti-human IgD as described above (see SDS-PAGE and detection of protein D on membranes). By comparison with the IgD-binding band on the membrane (Western blot) the appropriate band in the gel could be identified and cut out. Electrophoretic elution of the IgD-binding molecules (protein D) was performed and SDS was removed from the protein containing solution by precipitation in potassium phosphate buffer using a method from Susuki and Terrada (Anal. Biochem. 172:259, 1988). Potassium phosphate in a final concentration of 20 mM was added and after incubation at 4° C. overnight the SDS-precipitate was removed by centrifugation at 12,000 g. Thereafter the potassium content was adjusted to 60 mM and after 4 hrs at 4° C. centrifugation was performed as above. Finally the supernatant was concentrated and extensive dialysis was performed.

Dot Blot Assay

Proteins were applied to nitrocellulose membranes (Schleicher & Schuell, Dessel, West Germany) manually by using a dot blot apparatus (Schleicher & Schuell). After saturation, the membranes were incubated overnight at room temperature in 1% OA-TBS containing $^{125}$I-labeled protein probe (5 to $10 \times 10^5$ cpm/ml), washed four times with TBS containing 0.02% Tween-20, air dried, and autoradiographed at −70° C. by using Kodak CEA.C X-ray films and Kodak X-Omat regular intensifying screen (Eastman Kodak, Rochester, N.Y.).

Amino Acid Sequence Analysis

Automated amino acid sequence analysis was performed with an Applied Biosystems 470A gas-liquid solid phase sequenator (A) with online detection of the released amino acid phenylthiohydantoin derivatives by Applied Biosystems Model 120A PTH Analyzer.

Bacterial Strains, Plasmids, Bacteriophages and Media Used for Cloning of Protein D

*H. influenzae,* nontypable strain 772, biotype 2, was isolated from a nasopharyngeal swab at the Department of Medical Microbiology, Malmö General Hospital, University of Lund, Sweden. *E. coli* JM83 were used as recipient for plasmids pUC18 and pUC19 and derivatives thereof. *E. coli* JM101 and JM103 were used as hosts for M13mp18 and mp19 bacteriophages. *H. influenzae* was cultured in brain-heart infusion broth (Difco Lab., Inc. Detroit, Mich.) supplemented with NAD (nicotine adenine dinucleotide) and hemin (Sigma Chemical Co., St Louis, Mo.), each at 10 µg/ml. *E. coli* strains were grown in L broth or 2×YT media. L agar and 2×YT agar contained in addition 1.5 g of agar per liter. L broth and L agar were, when so indicated, supplemented with ampicillin (Sigma) at 100 µg/ml.

DNA Preparations

Chromosomal DNA was prepared from *H. influenzae* strain 772 by using a modification of the method of Berns and Thomas (J Mol. Biol. 11:476, 1965). After the phenol:chloroform:isoamylalcohol (25:24:1) extraction step the DNA was ethanol precipitated. The DNA was dissolved in 0.1×SSC (1×SSC:0.15 M NaCl and 0.015 M sodium citrate) and RNase treated for 2 h at 37° C. The RNase was removed with two chloroform:isoamylalcohol (24:1) extractions. The DNA was banded in a CsCl-ethidium bromide equilibrium gradient.

Plasmid DNA and the replicative form of phage M13 from *E. coli* JM101 were obtained by the alkaline lysis procedure followed by further purification in a CsCl-ethidium bromide gradient. In some cases plasmid DNA was prepared using a Quiagen plasmid DNA kit (Diagen GmbH Düsseldorf, FRG).

Single-stranded (ss) DNA from phage M13 clones was prepared from single plaques (Messing, J. Meth. Enzymol 101C:20, 1983).

Molecular Cloning of the Protein D Gene

A *H. influenzae* genomic library was constructed starting from 40 µg of *H. influenzae* strain 772 DNA which was partially digested with 1.2 units Sau3A for 1 h at 37° C. The cleaved DNA was fractionated on a sucrose gradient (Clark-Curtiss, J. E. et al., J. Bacteriol. 161:1093, 1985). Fractions containing DNA fragments of appropriate sizes (2–7 kilo-basepairs (kbp)) were pooled and the DNA was ligated to dephosphorylated BamHI digested pUC18 under standard conditions (Maniatis, T. et al., Molecular cloning: A laboratory manual, 1982). The ligation mixture was transformed into component *E. coli* JM83 by high voltage electroporation with a Gene Pulser™/Pulse controller apparatus, both from Bio-Rad Lab. (Richmond, Calif.). The bacteria were plated onto L agar supplemented with ampicillin and X-gal (5-Bromo-4-chloro-3-indolyl-β-D-galactopyranoside).

Colony Immunoassay

For colony immunoblotting, *E. coli* transformants, cultivated overnight on L agar, were transferred to nitrocellulose filters (Sartorius GmbH, Göttingen, FRG) by covering the agar surfaces with dry filters. The plates were left for 15 min before the filters were removed and exposed to saturated chloroform vapour for 15 min. Residual protein binding sites on the filters were blocked by incubating the filters in Tris balanced saline containing ovalbumine for 30 min (TBS-ova; 50 mM Tris-HCl, 154 mM NaCl, 1.5% ova.; pH 7.4). After blocking, the filters were incubated in turn with (i) culture supernatants containing mouse monoclonal antibodies (MAbs) directed against protein D at a dilution of 1:10 in TBS-ova, (ii) horseradish peroxidase conjugated rabbit anti-mouse IgGs (DAKOPATTS A/S, Glostrup, Denmark) in TBS-ova at a dilution of 1:2000 in TBS-ova, and (iii) 4-chloro-1-naphthol and $H_2O_2$. The filters were washed 3×10 min in wash buffer (TBS-0.05% Tween 20) between each step. All incubations were done at room temperature.

Colonies were also checked for IgD binding by incubating other filters with purified human myeloma IgD:s, rabbit anti-human IgD (δ-chains) (DAKOPATTS), horseradish peroxidase conjugated goat anti-rabbit Ig:s (Bio-Rad Lab.) and 4-chloro-1-naphthol and $H_2O_2$ as above.

Restriction Endonuclease Analysis and DNA Manipulations

Plasmid and phage DNA were digested with restriction endonucleases according to the manufacturers' instructions (Boehringer Mannheim mbH, Mannheim, FRG, and Beckman Instruments, Inc., England). Restriction enzyme fragments for subcloning were visualised with low energy UV-light and excised from 0.7–1.2% agarose gels (Bio-Rad) containing 0.5% ethidium bromide. The DNA bands were extracted with a Geneclean™ kit (BIO 101 Inc., La Jolla, Calif.) as recommended by the supplier.

Ligations were performed with 14 DNA ligase (Boehringer Mannheim) under standard conditions (Maniatis et al., 1982). The ligation mixtures were used to transform competent *E. coli* cells.

Progressive deletions of the recombinant plasmid pHIC348 for the sequencing procedure were produced by varying the time of exonuclease III digestion of KpnI-BamHI-opened plasmid DNA (Henikoff, S. Gene 28:351, 1984). For removal of the resulting single-stranded ends, mung bean nuclease was used. Both nucleases were obtained from Bethesda Research Laboratories Inc. (Gathersburg, Md.).

Protein D Extraction From *E. coli*

Cells of *E. coli* expressing protein D were grown in L broth supplemented with ampicillin to early logarithmic phase and then subjected to osmotic shock. After removal of periplasmic fraction the cells were lysed with NaOH (Russel, M. and Model, P., Cell 28:177, 1982) and the cytoplasmic fraction was separated from the membrane fraction by centrifugation. The periplasmic and cytoplasmic proteins were precipitated with 5% tri-chloro acetic acid.

DNA Sequencing and Sequence Manipulations

The nucleotide sequence was determined by direct plasmid sequencing (Chen, E. Y. and Seeburg, P. H. DNA 4:165, 1985) of subclones and deletion derivatives of plasmid pHIC348 using the chain termination method with $\alpha[^{35}S]$-dATP (Amersham) and Sequenase™, version 2 (United States Biochemical Corp., Cleveland, Ohio) following the protocol provided by the supplier. Part of the sequencing was done on single-stranded M13 DNA carrying inserts derived from pHIC348. Autoradiography was performed with Fuji X-ray film.

Results

Distribution of Protein D in *Haemophilus influenzae*

A total of 116 *H. influenzae* strains obtained from culture collections and freshly isolated from nasopharyngeal swabs were selected for IgD-binding experiments. Eleven of the strains were encapsulated representing serotypes a–f, and 105 strains were non-encapsulated (nontypable). These 105 strains belonged to biotype I (21 strains), biotype II (39 strains), biotype III (14 strains), biotype IV (2 strains) and biotype I (5 strains). Of the non-encapsulated strains 31 were not biotyped (NBT) but tested for IgD binding.

Approximately $4\times10^8$ cfu of *H. influenzae* bacteria grown on chocolate agar were mixed and incubated with 40 ng of radiolabeled human myeloma IgD. Thereafter a larger volume (2 ml) of PBS containing Tween 20 was added, bacteria were spun down and radioactivity of pellets was measured. All *H. influenzae* isolates bound IgD to a high degree (38–74%) (FIG. 1). There was no difference in IgD-binding capacity between different serotypes (a–f) of encapsulated *H. influenzae*. Nor was there any difference between different biotypes of non-encapsulated strains. 30 strains representing different sero- and biotypes were also grown in brain-heart infusion broth. When those bacteria grown in liquid medium were compared with the same bacteria grown on chocolate agar, no difference in IgD-binding capacity could be detected.

Protein D was solubilized from all 116 *H. influenzae* strains by sonication and Sarcosyl extraction. Subsequently the extracts containing protein D were subjected to SDS-PAGE. Proteins were stained or electroblotted onto nitrocellulose membranes and probed with human IgD myeloma protein and three different mouse monoclonal antibodies recognizing protein D. Many protein bands could be detected in all SDS-gels but electrophoresis of extracts from all *H. influenzae* isolates gave a protein band with an apparent molecular weight of 42,000 (42 kilodaltons). IgD and also all three anti-protein D monoclonal antibodies (16ClO, 20G6 and 19B4) bound to the same band after electrophoresis of all extracts and subsequent transfer to membranes and blotting.

Bacterial strains of 12 different species taxonomically related to *H. influenzae* (*H. ducreyi, H. paraphrophilus, H. parasuis, H. parainfluenzae, H. haemolyticus, H. parahaemolyticus, H. aphrophilus, H. segnis, H. aegypticus, H. haemoglobinophilus, E. corrodens, A. actinomycetemcomitans*) were tested for their capacity to bind $^{125}$I labeled human IgD. In addition crude Sacrosyl extracts from the same bacteria were tested by Western blot analysis with IgD and the three anti-protein D monoclonal antibodies (MAbs 16ClO, 20G6, 19B4).

Figure 2:
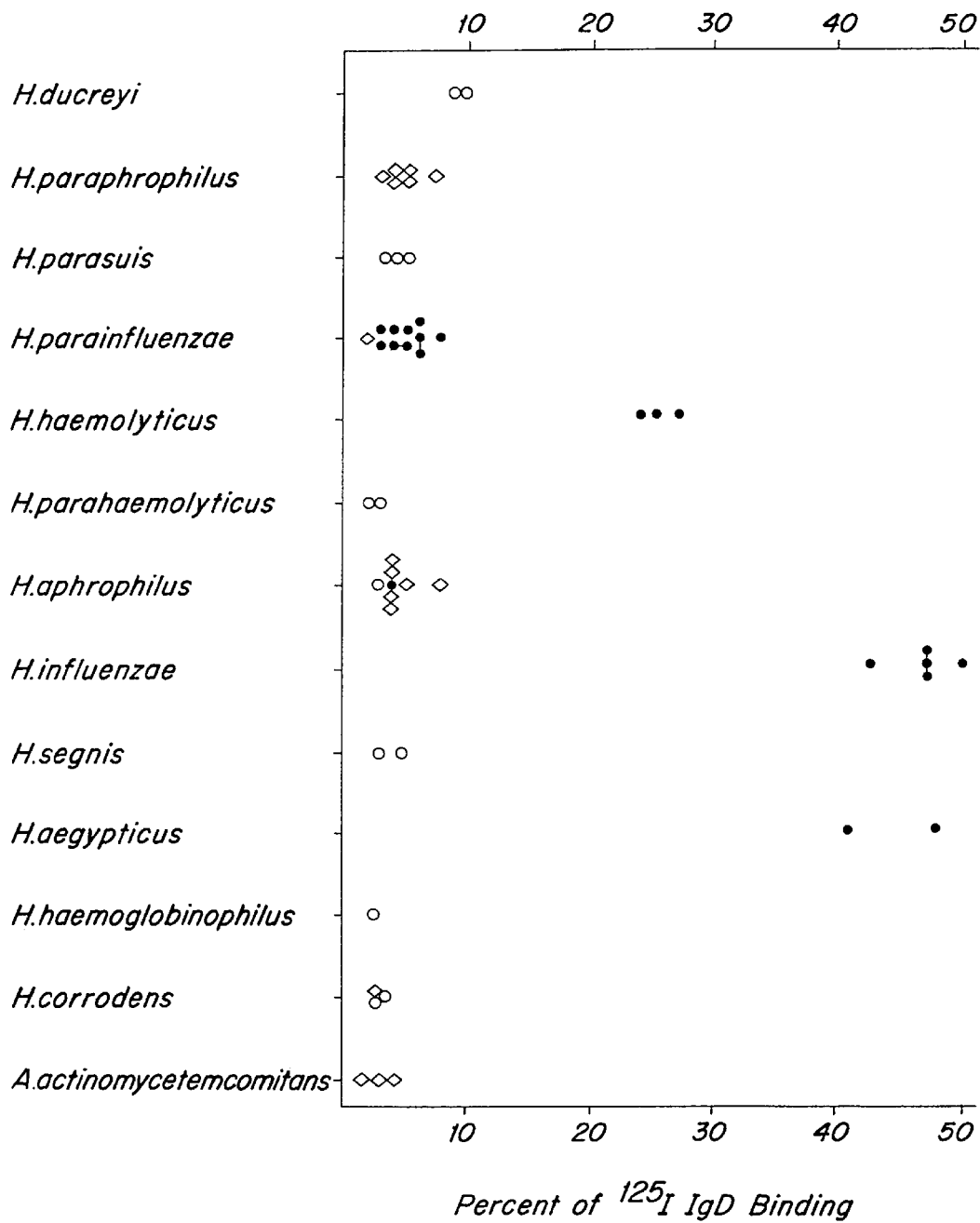
FIG. 2 is a direct binding assay demonstrating that of the bacteria tested, only *H. haemolyticus* and *H. aegypticus* bound radiolabeled IgD.

Of all twelve species tested, only *H. haemolyticus* (5/5 strains) and *H. aegypticus* (2/2 strains) bound radiolabeled IgD, 21–28% and 41–48%, respectively, in the direct binding assay (FIG. 2). In Western blot analysis IgD and all three monoclonal antibodies detected a single band with an apparent molecular weight of 42,000 (42 kilodaltons).

None of the 6 strains of *H. paraphrophilus*, 11 *H. parainfluenzae*, 8 *H. aphrophilus*, and 3 *A. actinomycetemcomitans* bound radiolabeled IgD in the direct binding assay or reacted with IgD in Western blot analysis. However, extracts of all these strains reacted with two or three of the monoclonal antibodies in Western blot analysis showing a single 42 kilodaltons protein band. Western blot analysis of three strains of *E. corrodens* revealed a single high molecular weight band (90 kilodaltons) with MAb 16ClO in all three strains. In an extract of one of the strains, a single 42 kilodaltons band was detected with the two other monoclonal antibodies. Two strains of *H. ducreyi, H. parasuis* (2 strains), *H. parahaemolyticus* (2 strains), *H. sengius* (2 strains), *H. haemoglobinophilus* (1 strain) did not bind radiolabeled IgD in the direct binding assay and Sarcosyl extracts from the same bacteria did not reveal any protein band detectable by IgD or the three monoclonal antibodies.

Solubilization of Protein D

Figure 3:
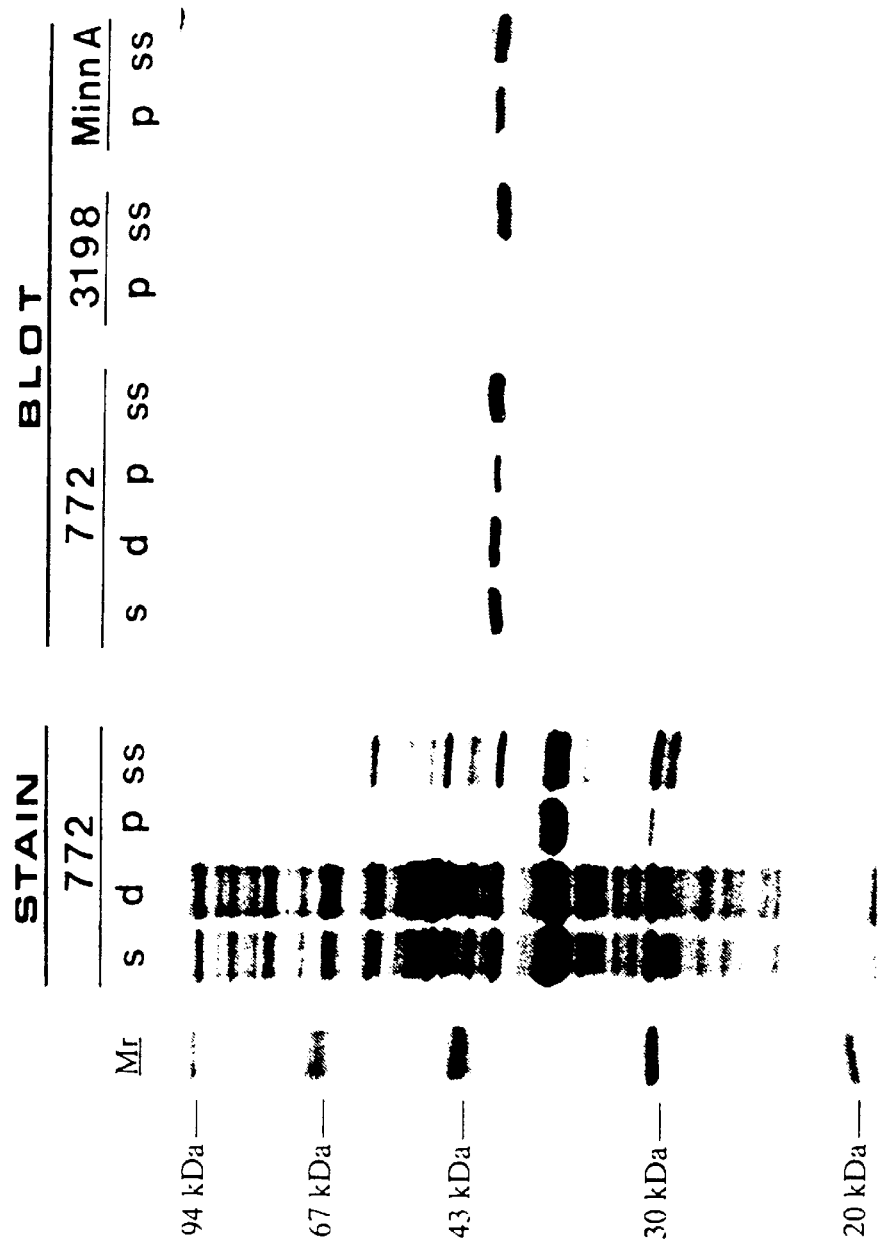
FIG. 3 depicts stains and electroblots of solubilized proteins.

Three different strains of *H. influenzae* (two nontypable strains, 772 and 3198 and one type B, Minn A.) were grown overnight in broth. Initially attempts were made to solubilize protein D according to a well established method for isolation of *H. influenzae* outer membrane proteins by sonication, removal of the cell debris by centrifugation and extraction of the supernatant with Sarcosyl followed by ultracentrifugation (Barenkamp S J and Munson R S J Infect Dis 143:668, 1981). The pellets (cell debris) (d) and supernatants (s) after sonication as well as the pellets (p) and supernatants (ss) after Sarcosyl-treatment and ultracentrifugation were subjected to SDS-PAGE. Proteins were stained or electroblotted onto Immobilon membranes and probed with human IgD myeloma protein followed by incubation with peroxidase conjugated anti-human IgD-antibodies and substrate. As shown in FIG. 3 the sonication procedure solubilized proteins including protein D effectively. However, IgD-binding molecules (protein D) could also be detected in the cell debris, i.e. were not solubilized by sonication. The yield of IgD-binding molecules in the supernatant varied between different experiments. FIG. 3 also shows that protein D mostly could be detected in the Sarcosyl soluble supernatant after ultracentrifugation. In contrast previously described outer membrane proteins of *H. influenzae* (protein 1 to 6) are readily solubilized by sonication and are considered Sarcosyl insoluble.

Figure 4:
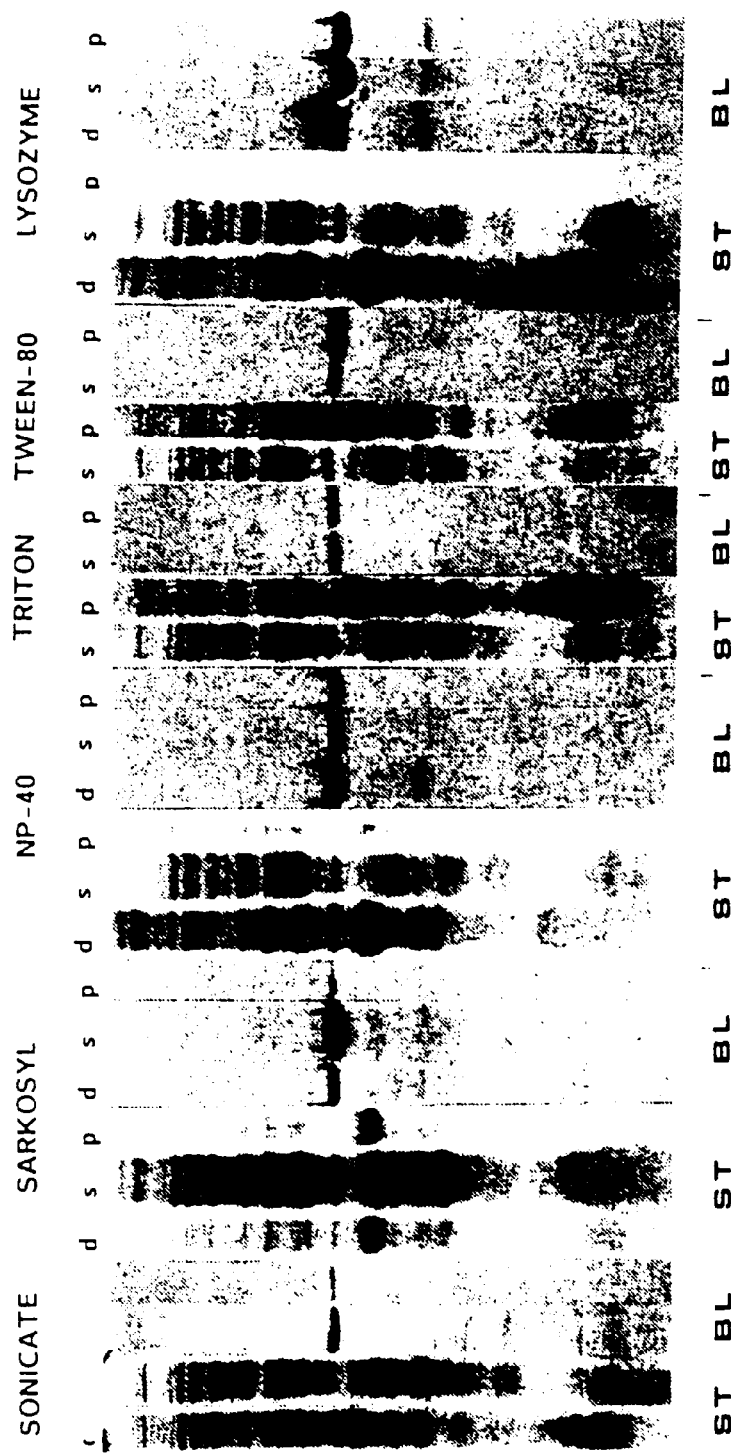
FIG. 4 depicts electrobots of cell debris which were probed with IgD demonstrating the Sarkosyl treatment effectively solubilized protein D.

To improve the yield of protein D several extraction methods were tried. In subsequent experiments the bacterial cells were sonicated and the whole cell suspension sonicated and extracted in different detergents (Sarcosyl, NP-40, Triton X-100 and Tween 80). The cell debris was removed by centrifugation (12,000 g) and the supernatant ultracentrifuged. The thus obtained cell debris (d), supernatants (s) and pellets (p) were analysed by SDS-PAGE, electroblotting onto membranes and subsequent probing with IgD. As shown in FIG. 4 Sarcosyl treatment effectively solubilized protein D leaving little left in the cell debris and pellet. NP-40, Triton X-100 and Tween-80 solubilized protein D less effectively.

Attempts were also made to solubilize protein D from the bacteria with lysozyme and different proteolytic enzymes (papain, pepsin and trypsin) at different concentrations. Of the enzymes only lysozyme solubilized protein D (FIG. 4).

Purification of Protein D

Protein D was solubilized by Sarcosyl extraction of whole bacteria as described above and purification was performed by SDS-PAGE of the supernatant after ultracentrifugation. After electrophoresis narrow gel strips were cut out, proteins were transferred to membranes and the IgD-binding band (protein D) was detected by Western blot assay. Gel slices containing a protein band corresponding to the IgD-binding molecules were cut out from the gel and solubilized by electronic elution. At reelectrophoresis the purified protein, protein D (D), migrated as a single band (42 kilodaltons) (FIG. 5) without discernible breakdown products.

Figure 5:
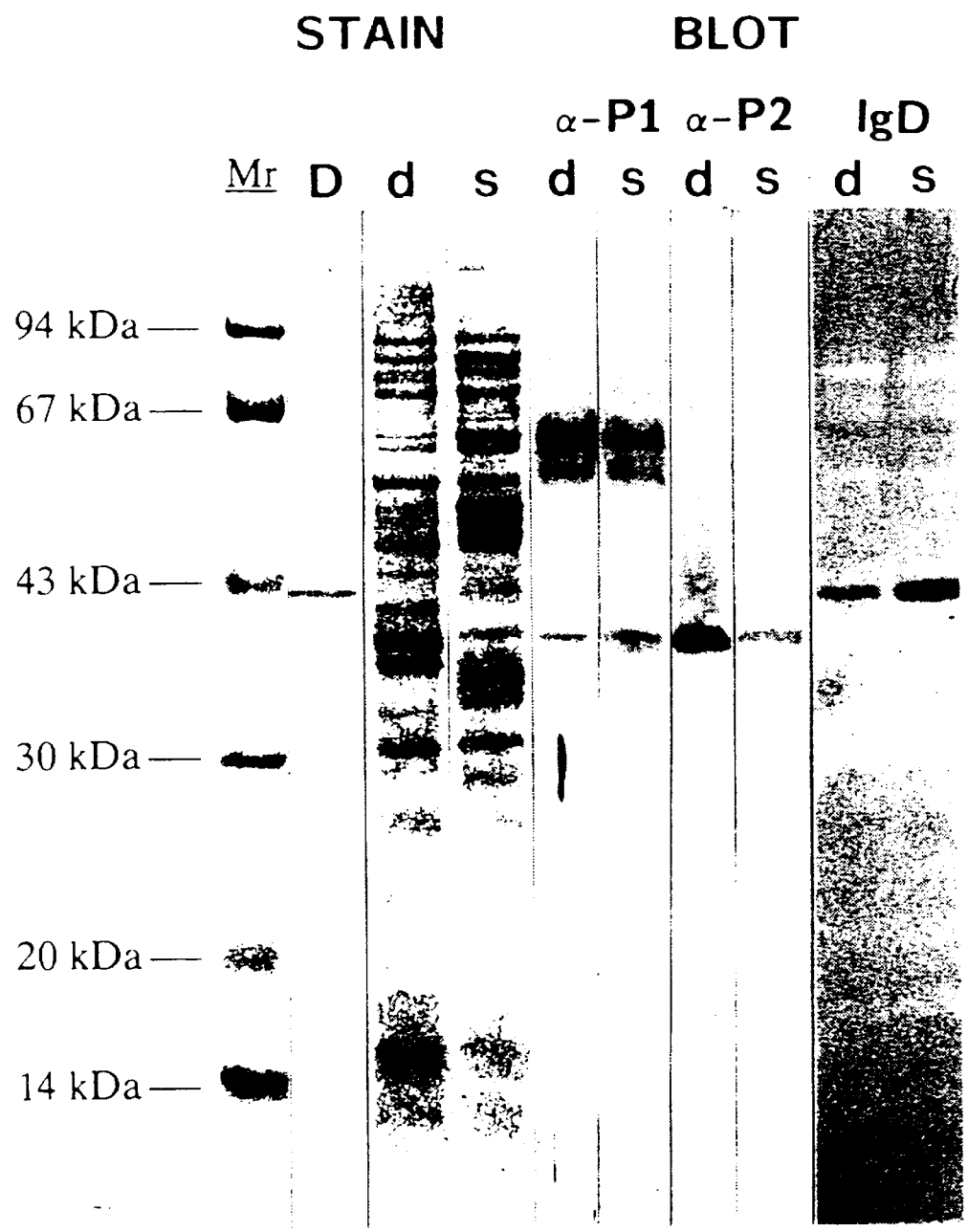
FIG. 5 depicts a reelectrophoresis of purified protein D.

To confirm that protein D was not identical with the previously described outer membrane proteins 1 or 2 with molecular weights of 49 and 39 kilodaltons, respectively, debris (d) and supernatants (s) after Sarcosyl extraction of whole *H. influenzae* bacteria were subjected to SDS-PAGE, transferred to Immobilon filters and blotted with antibodies to protein 1 and protein 2 and also with human IgD. As can be seen in FIG. 5 protein D migrates differently from protein 1 and protein 2.

Binding Properties of Protein D

Figure 6A:
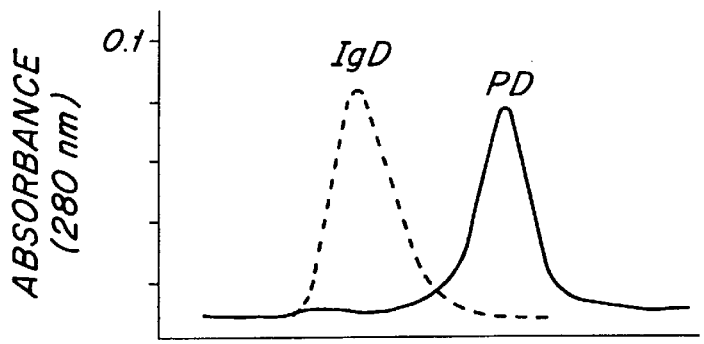
FIGS. 6A, 6B, 6C, and 6D are graphs ehich depicts the interaction of protein D with human IgD when the proteins were run on a Sephadex G-200 column.
Figure 6B:
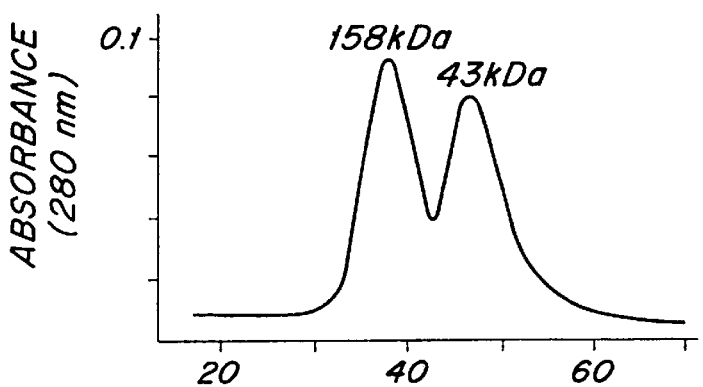
Figure 6C:
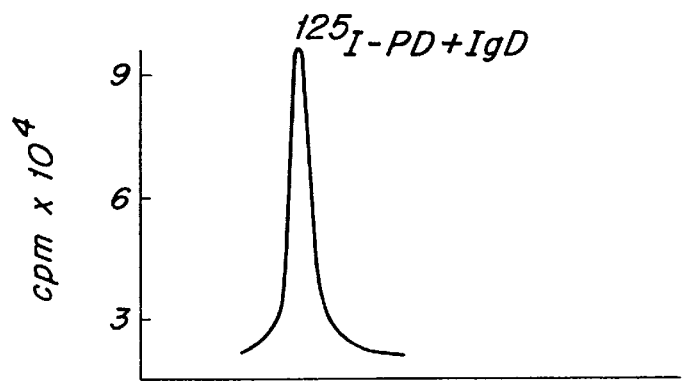
Figure 6D:
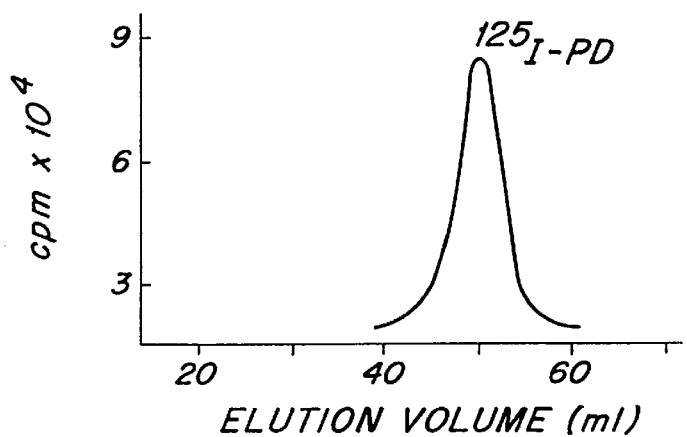

The interaction of protein D with human IgD was further verified in gel filtration experiments where $^{125}$I-protein D was eluted together with IgD when a mixture of the two proteins was run on a Sephadex G-200 column (FIG. 6c). Protein D run alone on the same column was eluted slightly after the 43 kilodaltons standard protein (Ovalbumin) confirming the apparent molecular weight of 42 kilodaltons for protein D.

Figure 7:
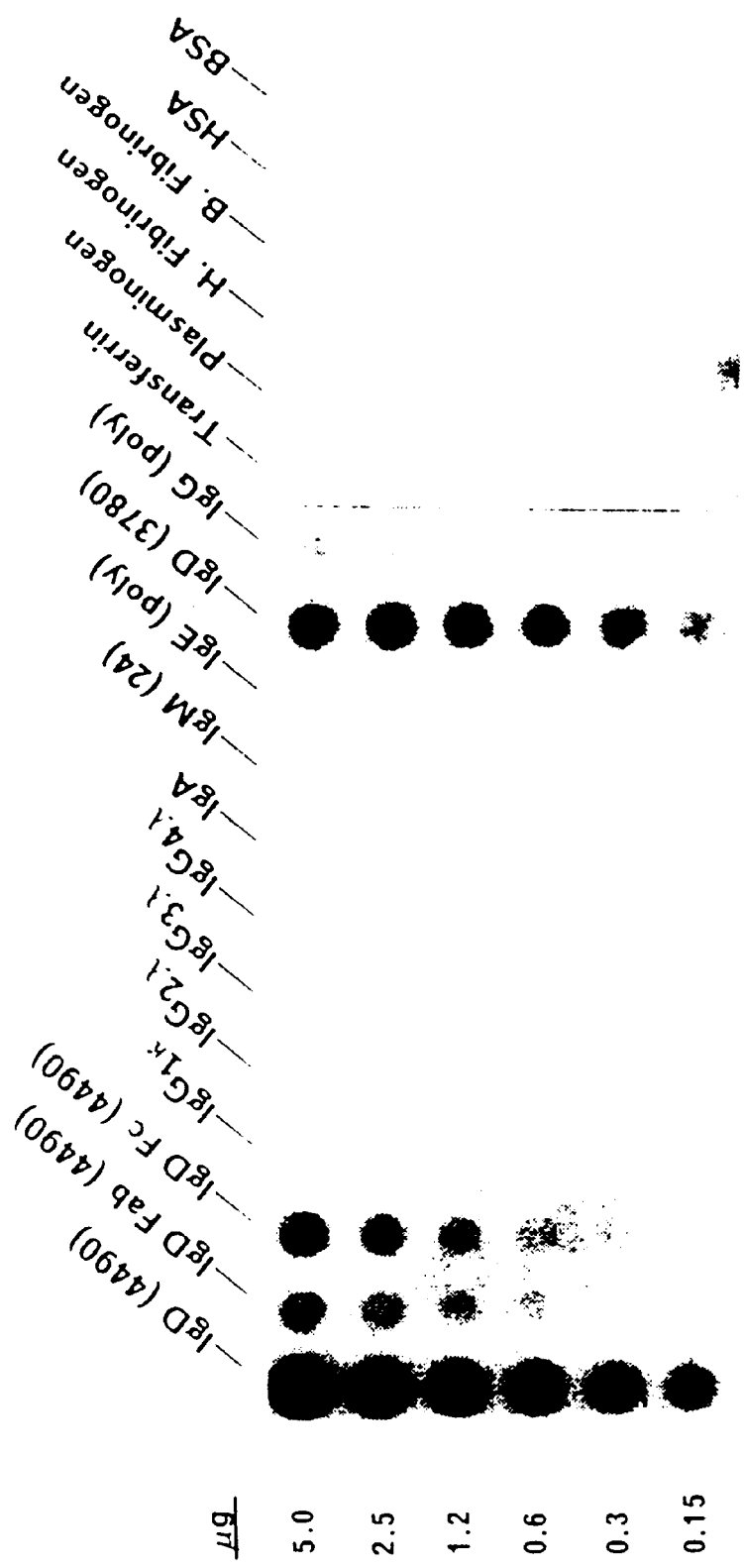
FIG. 7 is a dot blot which shows that protein D effectively bound to highly purified human IgD myeloma proteins.

Radiolabeled protein D was also studied in different dot blot experiments to further examine the binding specificity of the molecule. FIG. 7 shows that protein D effectively bound two highly purified human IgD myeloma proteins. A distinct reaction could be detected at 0.15 and 0.3 μg of the two IgD proteins, respectively. Two additional IgD myeloma proteins which were tested with the same technique could also distinctly be detected at 0.3 μg (data not shown). In dot blots IgD-Fab fragments and IgD-Fc fragments bound protein D at 2.5 and 1.2 μg, respectively. In contrast 8 different IgG myeloma proteins representing all subclasses and L-chain types showed no visible reaction with protein D at 5 μg. Neither could any reaction between protein D and three monoclonal IgM, one monoclonal IgA preparation, polyclonal IgE or some additional proteins be detected. However, with polyclonal IgG a weak reaction was detected at 5 μg (FIG. 7).

Cloning of the Protein D Gene

DNA isolated from *H. influenzae* 772 was partially digested with Sau3A and enriched for fragments in the size of 2 to 7 kilobasepairs (kbp) by fractionation on a sucrose gradient. These fragments were ligated to the BamHI-cut and phosphatase-treated vector pUC18. *E. coli* JM83 cells transformed with the ligation mixture by high voltage electroporation were plated selecting for resistance to ampicillin. Individual colonies were transferred to nitrocellulose filters and screened with a cocktail of monoclonal antibodies (MAbs) as described in.

Materials and Methods

Among the 15,000 colonies tested, 60 were found positive. Eight positive colonies were picked, purified and subjected to another two rounds of screening. All clones remained positive during the purification. The purified clones were tested for IgD binding with human IgD, rabbit anti-human IgD and peroxidase conjugated goat anti-rabbit Ig:s in a colony immunoassay as described in Materials and Methods. All were positive regarding IgD binding. Additionally, the clones were found positive when screening with the three MAbs individually.

Figure 8:
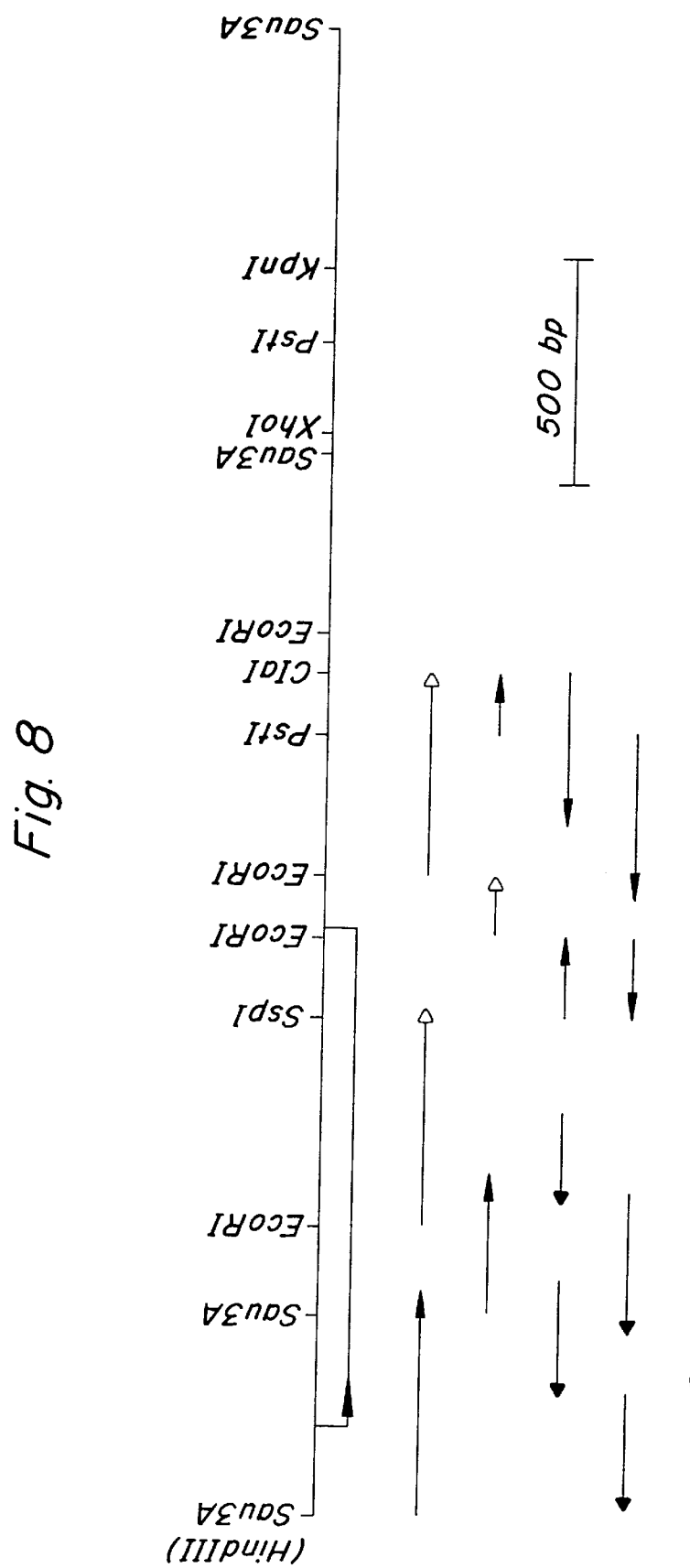
FIG. 8 is a partial restriction enzyme map for the insert of *H. influenzae* DNA in pHIJ32.

Restriction enzyme analysis of plasmid DNA from the positive clones showed that all but one clone carried a 3.3 kbp insert with two internal Sau3A sites. One clone contained an additional 2.0 kbp Sau3A fragment. One of the smaller recombinant plasmids, pHIJ32, was chosen for further characterization. A partial restriction enzyme map was established for the insert of *H. influenzae* DNA in pHIJ32 (FIG. 8). To identify the region coding for protein D, restriction enzyme fragments were subcloned into pUC18. The resulting transformants were tested for expression of protein D using colony immunoblot analysis as described above. These experiments showed that plasmids carrying a 1.9 kbp HindIII-ClaI fragment from one end of the insert allowed expression of IgD-binding protein. This recombinant plasmid, called pHIC348, was kept for further experiments. The protein D gene cloned in pHIC348 is expressed from a promoter in pUC18. This was shown by cloning the HindIII-ClaI fragment of pHIJ32 in the opposite orientation in pUC19. All transformants expressed IgD binding, as would be expected if the gene is under the control of an endogenous promoter. Transformants carrying the HindIII-ClaI fragment in the opposite direction to pHIC348 grew poorly and autolysed during cultivation. This was probably due to the lacZ promoter of pUC19 being oriented in the same direction as the promoter of protein D which led to an overexpression of protein D which was lethal to the cells. In pHIC348 the lacZ promoter was in the opposite direction of the protein D promoter.

DNA Sequence Analysis of the Protein D Gene

The nucleotide sequence of both strands of the insert from pHIC348 was determined either by direct plasmid sequencing of subclones and deletion constructs or by subcloning restriction fragments into phages M13mp18 and M13mp19. Commersially available universal and reverse M13 primers were used. Sequencing was done across all restriction enzyme sites used in subcloning and the sequencing strategy is outlined in FIG. 8.

The DNA sequence (FIG. 9) reveals an open reading frame of 1092 bp starting with an ATG codon at position 204 and finishing at position 1296 with a TAA stop codon. The open reading frame corresponds to a protein of 364 amino acid residues. Ten nucleotides upstream of the methionine codon is a sequence, AAGGAG, that is complementary to the 3' end of the 16S rRNA of *E. coli* (Shine, J. and Dalgarno, L. Proc. Natl. Acad. Sci. U.S.A., 71:1342, 1974). The spacing between the centre of this putative ribosome-binding site (rbs) and the start codon is 13 bp in comparison to the average spacing of 10 bp in *E. coli*. The 5' flanking region, upstream of the proposed rbs, shows the presence of possible promoters. The sequences of the −10 region, TAAAAT (151–156), and the −35 region, TTGCTT (127–132), show homology to the consensus of *E. coli* promoters (Rosenberg, M. and Court, D., Annu. Rev. Genet, 13:319, 1979) and are identical with promoters recognized by the *E. coli* RNA polymerase. The spacing between the putative −10 and −35 sequences is 18 bp, which is comparable with the favoured value of 17 bp.

Between position 1341 and 1359 there is an inverted repeat with the potential to form a stem and loop structure. This repeat does not, however, resemble a typical rho-independent transcription terminator.

Protein D Structure

The gene for protein D encodes for a protein of 364 amino acid residues deduced from the nucleotide sequence (FIG. 9). The N-terminal amino acid sequence has typical characteristics of a bacterial lipoprotein signal peptide (Vlasuk et al., J. Biol. Chem. 258:7141, 1983) with its stretch of hydrophilic and basic amino acids at the N-terminus followed by a hydrophobic region of 13 residues, and with a glycin in the hydrophobic core. The putative signal peptide ends with a consensus sequence Leu-Ala-Gly-Cys, recognized by the enzyme signal peptidase II (SpaseII). The primary translation product has a deduced molecular weight of 41,821 daltons. Cleavage by SpaseII would result in a protein of 346 amino acids with a calculated molecular size of 40,068 daltons, in contrast to the estimated size of the mature protein D of approximately 42 kilodaltons. Post-translational modifications of the preprotein may account for this discrepancy. Several attempts to determine the amino-terminal amino acid sequence of protein D were performed by applying about 1000 pmoles thereof in an automated amino acid sequencer. Since no amino acid phenylthiohydantoin derivatives were obtained, the amino-terminal end of the single IgD-receptor polypeptide chain is probably blocked.

Figure 10:
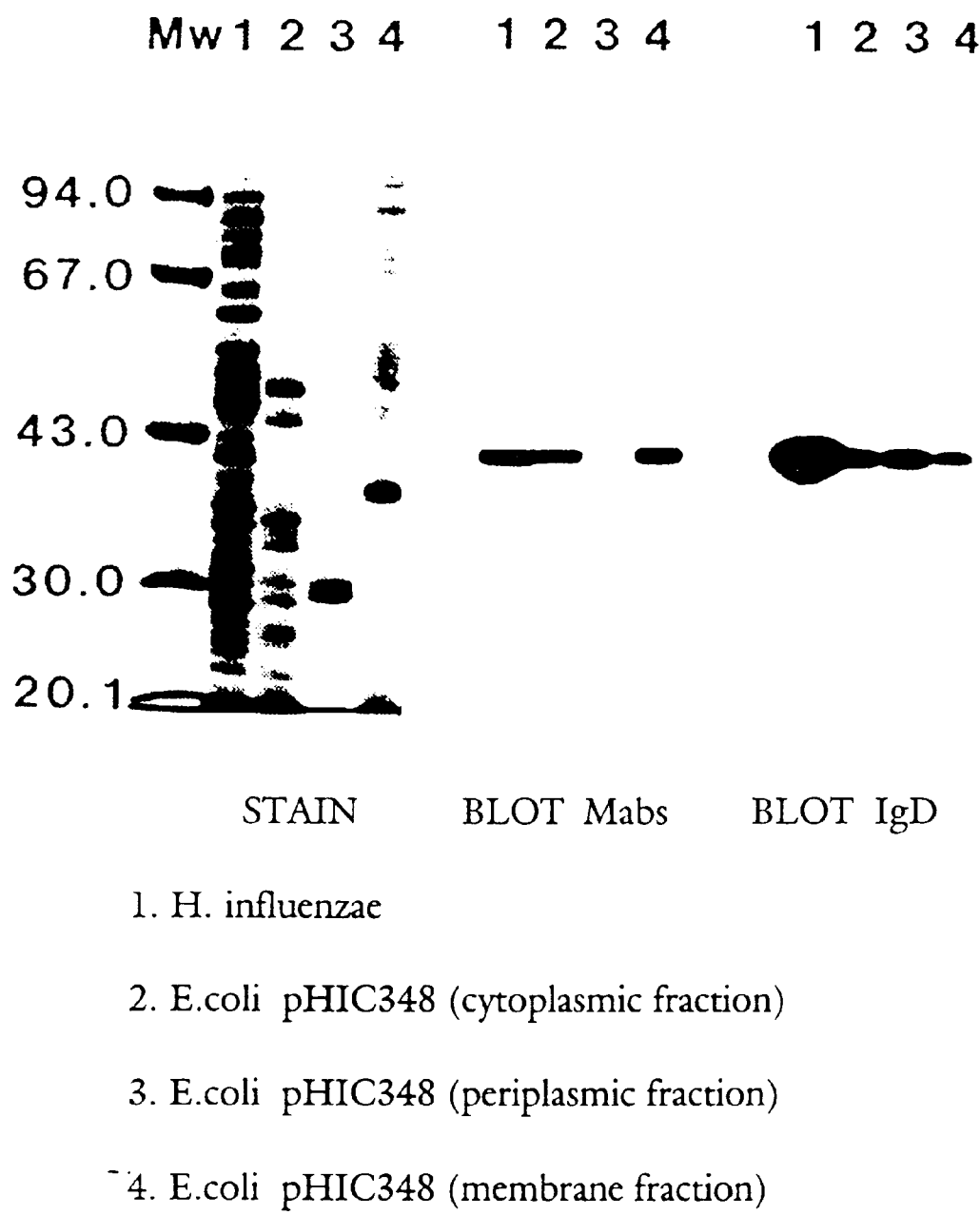
FIG. 10 depicts an immunoblotting experiment which analyzed protein D expressed in *E. coli* JM83 carrying pHIC348.

Protein D expressed in *E. coli* JM83 carrying pHIC348 was analysed in immunoblotting experiments (FIG. 10). Cytoplasmic, periplasmic and membrane fractions from cells in late logarithmic phase were separated on a SDS-PAGE gel and electroblotted to an Immobilon filter. A protein that binds all three anti-protein D monoclonal antibodies (16ClO, 20G6 and 19B4) and radiolabeled IgD could be detected in all three fractions (lane 2–4) from *E. coli* JM83/pHIC348 as a single band with an estimated molecular weight of 42 kilodaltons, i.e. equal or similar to protein D prepared from *H. influenzae* (lane 1, FIG. 10).

The nucleotide sequence and the deduced amino acid sequence of *H. influenzae* 772 protein D were compared with other proteins of known sequence to determine homology by using a computer search in the EMBL and Genbank Data Libraries. Apart from similarities in the signal sequence no homology was found.

SUMMARY

A novel surface exposed protein of *H. influenzee* or related Haemophilus species is described. The protein named protein D is an Ig receptor for human IgD and has an apparent molecular weight of 42,000. Protein D can be detected in all of 116 encapsulated and non-encapsulated isolates of *H. influenzae* studied. The protein from all strains shows in addition to the same apparent molecular weight immunogenic similarities since protein D from all strains interacts with three different mouse monoclonal antibodies and monoclonal human IgD. A method for purification of protein D is described. Cloning of the protein D gene from *H. influenzae* in *E. coli* is described as well as the nucleotide sequence and the deduced amino acid sequence corresponding to a molecular weight of 41,821 daltons including a putative signal sequence of 18 amino acids containing a consensus sequence, Leu-Ala-Gly-Lys for bacterial lipoproteins.

---

What is claimed is:

1. A purified and isolated peptide consisting of an immunogenic portion of protein D, wherein protein D has an apparent molecular weight of 42,000, as determined by SDS-PAGE under reducing conditions by comparison to molecular weight standards, and is encoded by the DNA sequence of SEQ ID NO: 1.

2. A purified and isolated fusion protein or polypeptide in which the immunogenic portion of protein D of claim 1 is combined with another polypeptide using recombinant DNA technology.

3. An immunogenic composition comprising the fusion protein or polypeptide of claim 2 and a pharmaceutical carrier.

4. A fusion product in which the immunogenic portion of protein D of claim 1 is covalently bound to a protein, carbohydrate or matrix.

5. An immunogenic composition comprising the fusion product of claim 4 and a pharmaceutical carrier.

6. An immunogenic composition comprising the immunogenic portion of protein D of claim 1 and a pharmaceutical carrier.

7. A fusion product in which the immunogenic portion of protein D of claim 1 is bound to a protein or carbohydrate.

8. An immunogenic composition comprising the fusion product of claim 7 and a pharmaceutical carrier.

* * * * *